(12) United States Patent
Porter et al.

(10) Patent No.: US 6,911,451 B1
(45) Date of Patent: Jun. 28, 2005

(54) PHENYLALANINE DERIVATIVES

(75) Inventors: John Robert Porter, Chinnor (GB); John Clifford Head, Maidenhead (GB); Graham John Warrellow, Northwood (GB); Sarah Catherine Archibald, Maidenhead (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/326,020

(22) Filed: Jun. 4, 1999

(30) Foreign Application Priority Data

Jun. 5, 1998 (GB) ............................................ 9812088

(51) Int. Cl.$^7$ ...................... A61K 31/435; A61K 31/44; A61K 31/445; C07D 211/78; C07D 211/72
(52) U.S. Cl. ...................... 514/277; 514/354; 514/323; 514/344; 514/346; 514/349; 514/350; 514/351; 546/287; 546/288; 546/290; 546/291; 546/293; 546/300; 546/301; 546/304; 546/305; 546/329; 546/349
(58) Field of Search .................................. 514/342, 354, 514/277, 344, 346, 350, 357, 349, 351; 546/323, 340, 290, 288, 289, 293, 305, 300, 342, 287, 291, 301, 304, 329, 349

(56) References Cited

U.S. PATENT DOCUMENTS

| | | | |
|---|---|---|---|
| 4,470,973 A | 9/1984 | Natarajan et al. | 424/177 |
| 4,554,273 A | 11/1985 | Bayssat et al. | 514/221 |
| 4,987,132 A | 1/1991 | Mase et al. | 514/252 |
| 5,164,372 A | 11/1992 | Matsuo et al. | 514/19 |
| 5,206,373 A * | 4/1993 | Chung et al. | 546/335 |
| 5,260,277 A | 11/1993 | McKenzie | 544/18 |
| 5,296,486 A | 3/1994 | Lazer et al. | 514/333 |
| 5,399,585 A | 3/1995 | Alig et al. | 514/438 |
| 5,510,346 A | 4/1996 | Martin et al. | 514/221 |
| 5,698,691 A | 12/1997 | Yukimasa et al. | 540/490 |
| 6,093,696 A | 7/2000 | Head et al. | 514/19 |
| 6,596,752 B1 * | 7/2003 | Lobl et al. | 514/401 |

FOREIGN PATENT DOCUMENTS

| | | | |
|---|---|---|---|
| DE | 23 16 881 A | | 10/1973 |
| DE | 28 37 264 A1 | | 3/1979 |
| DE | 196 54 483 A | | 1/1998 |
| EP | 0 144 230 A | | 6/1985 |
| EP | 0 498 268 A2 | | 8/1992 |
| EP | 0 596 406 A1 | | 5/1994 |
| EP | 0 710 657 A1 | | 5/1996 |
| EP | 0 710 659 A1 | | 5/1996 |
| EP | 0 842 943 A2 | | 5/1998 |
| EP | 0 842 945 A2 | | 5/1998 |
| JP | 56 090045 | | 7/1981 |
| JP | 61083161 | * | 4/1986 |
| JP | 03 135962 | | 6/1991 |
| JP | 63233963 | * | 4/1995 |
| JP | 63-233963 | * | 9/1999 |
| WO | WO 93/00095 | | 1/1993 |
| WO | WO 93/08174 | | 4/1993 |
| WO | WO 93/09795 | | 5/1993 |
| WO | 9316994 | * | 9/1993 |
| WO | WO 94/29285 | | 12/1994 |
| WO | WO 9509828 | * | 4/1995 |
| WO | WO 95/19356 | | 7/1995 |
| WO | WO 96/26190 | | 8/1996 |
| WO | WO 97/12866 | | 4/1997 |
| WO | 9724122 | * | 7/1997 |
| WO | WO 97/24124 | | 7/1997 |
| WO | WO 97/36859 | | 10/1997 |
| WO | WO 98/00395 | | 1/1998 |
| WO | WO 98/42662 | | 10/1998 |
| WO | WO 98/54207 | | 12/1998 |
| WO | 9906435 | * | 2/1999 |
| WO | WO 99/35163 | | 7/1999 |
| WO | WO 99/37618 | | 7/1999 |
| WO | WO 99/43642 | * | 9/1999 |
| WO | WO 99/48879 | | 9/1999 |
| WO | WO 00/31067 | | 6/2000 |
| WO | WO 00/35855 | | 6/2000 |

OTHER PUBLICATIONS

Bolin, et. al., Structure–activity studies on the vasoactive intestinal peptide pharmacophore, Int. J. Peptide Res. 46, pp. 279–289, 1995.*

Ca 124:56589, "Polymer–supported Mitsunobo ether formation and its use in combinatorial chemistry", Krchnak et. al., p. 1.*

Ca 86:107036, "Amino–acids and peptides. Part XL. Protection removable by electrolytic reduction: the use of S–4–picolyl–L–cystene and O–4–picolyl–L–tyrosine in synthesis.", p. 1.*

(Continued)

*Primary Examiner*—Joseph K. McKane
*Assistant Examiner*—Binta Robinson
(74) *Attorney, Agent, or Firm*—Woodcock Washburn LLP

(57) ABSTRACT

Phenylalanine derivatives of formula (1) are described:

$$R^1(Alk^1)_r(L^1)_s \text{—} \underset{\underset{R}{|}}{\overset{}{\text{—}}} \text{—} (Alk^2)_m \quad C(R^2)X^1R^4 \qquad (1)$$

wherein
L$^1$ is a linker atom or group;
X$^1$ is a group selected from —N(R$^3$)CO—, —N(R$^3$)SO$_2$—, —N(R$^3$)C(O)O— or
—N(R$^3$)CON(R$^{3a}$)—; and
R is a carboxylic acid or a derivative thereof.

The compounds are able to inhibit the binding of a 4 integrins to their ligands and are of use in the prophylaxis and treatment of diseases or disorders involving inflammation.

9 Claims, No Drawings

OTHER PUBLICATIONS

Chung et. al., "A Practical Synthesis of Fibrinogen Receptor Antagonist MK–383. Selective Functionalization of (S)–Tyrosine", Tetrahedron, vol. 49, No. 26, pp. 5767–5776.*

Azzouny, A.E., et al., "Synthesis of some N–substituted salicylamides structurally related to certain antimicrobials," Pharmazie, 1977, 32(6), 318–323 (abstract).

Badshah, A., et al., "Catalytic reduction of azlactones in alkaline media. Synthesis of amino acids," J. of Organic Chemistry, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," J. of Medicinal Chemistry, 1990, 33(6), 1620–1634.

Rico, J.G. et al., "A highly stereoselective michael addition to an $\alpha$, $\beta$–unsaturated ester as the crucial step in the synthesis of a novel beta–amino acid–containing fibrinogen receptor antagonist", J. Org. Chem, 1993, vol. 58, pp. 7948–7951.

Zablocki, J.A. et al., "Potent in vitro and in vivo inhibitors of platelet aggregation based upon the Arg–Gly–Asp sequences of fibrinogen", J. Med. Chem., 1995, vol. 38, pp. 2378–2394.

Bach et al., "Anomalous optical rotation and circular dichroism of N–thioacylated.alpha.–amino acids and deriva," Acta Chem. Scand., 1966, 20(10), 2781–2794.

Barrett, G.C., "Circular dichroism of N–thiobenzoly–1–$\alpha$–amino acids. III. Their circular dichroism through the near–ultraviolet wavelength range," J. Chem. Soc., 1967, Section C, 1–5.

Chemical Abstracts, "N–[4–Thiazolidinyl)carbonyl]amino acid derivatives," 1981, 95(19), Abstract No. 169173f, 1 page.

Cornforth, J. W., "Oxazoles and Oxazolones," Chem. Penicillin, Princeton Book Review, 1949, pp. 688, 799, and 800.

Fu, H. et al., "Preliminary study on synthesis and antitumor activity in vitro of derivatives of timonacic," Chemicals Abstracts, 1988, 108(17), Abstract No. 150358k, 1 page.

Harris, R.L.N. et al., Aust. J. Chem., "Potential wool growth inhibitors. 2(1H)–Pyridone analogs of mimosine," 1977, 30(3), 649–655.

Hartke, K. et al., "Dithio and thiono esters. Part 61. Synthesis of $\alpha$–amino dithioesters and endothiodipeptides,", J. Prakt. Chem. 1996, 338(3), 251–256.

Jaynes, B.H. et al., "Synthesis and In Vivo Antibacterial Activity of Hygromycin a Analogs Modified at the $C_4$' Aryl Position," Bioorg. Med. Chem. Letts., 1993, 3(8), 1531–1536.

Jepson, J.B. et al., "Reactions of $\alpha$–Thioacylamino–acids. Their conversion into Thiazolones and Derivatives Thereof," J. Chem. Soc., 1955, 1791–1797.

Masahiko, N., Japanese Patent No. 57–080370 published May 19, 1982, "Alpha–Methylcinnamic Acid Derivative, its Preparation and Antilipemic Agent Containing The Same," Patent Abstracts of Japan, 1982, 1 page.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," Yakugaku Zasshi, 1959, 79(12), 1514–1518 (English summary included).

Ohki, S. et al., "Synthesis of quinolizine derivatives. V. Studies on Diastereoisomer of Ethyl 3–Quinolizidinecarboxylate," Chem. Pharm. Bull., 1959, 7(6), 708–712.

Schultz, Von O.–E. et al., "Analogos of nuleic acid based as antimetabolites," Arzneimittel Forschung. Drug Res., 1967, 17(8), 1060–1064 (English summary included).

Tsunematsu, H. et al., "Hydrolysis of phenylthiazolones of p–guanidinophenylalanine and arginine by trypsin and related enzymes," J. Biochem., 1983, 94(4), 1119–1125.

Whitlock, B.J. et al., "Structure and synthesis of lathyrine," J. Org. Chem., 1965, 30, 115–118.

Hammadi, A., et al., "Diastereoselective hydrogenation of monodehydro enkephalins controlled by chiral rhodium catalysts," Tetrahedron: Asymmetry, 1992, 3(10), XP002106601, 1247–1262.

Nunami, K., et al., "A novel synthesis of methyl 1,5–disubstituted imidazole–4–carboxylates using 3–bromo–2–isocyanoacrylates," J. Org. Chem., 1994, 59, XP002106602, 7635–7642.

Shimohigashi, Y., et al., "Dehydro–enkephalins," Int. J. Peptide Protein Res., 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," J. Chem. Soc., Perkin I, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Buckle, D.R., et al., "Non Thiazolidinedione Antihyperglycaemic Agents. 1: $\alpha$–Heteroatom Substituted $\alpha$–Phenylpropanoic Acids," Bioorg. Med. Chem. Lett., 1996, 6(17), 2121–2126.

Keenan, R.M. et al., "Discovery of Potent Nonpeptide Vitronectin Receptor (av$\beta_3$) Antagonists," J. Med. Chem., 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," J. Am. Chem. Soc., 1994, 116, 5077–5983.

Miller, W.H. et al., "Structure–Activity Relationships in 3–Oxo–1,4–Benzodiazepine–2–Acetic Acid GPIIb/IIIa Antagonists. The 2–Benzazepine Series," Bioorg. Med. Chem. Lett., 1996, 6(21), 2481–2486.

Ukai, Y. et al., "A novel synthetic inhibitor of endopeptidase–24.15," Chemical Abstracts, 1997, 127(2), 1 page.

Venturella, V.S. et al., "Substituted 1,3–Dihydro–4H–furo [3,4–d]–1,3–benzodiazepin–3–ones: Synthesis and Scope of the Method," J. Heterocyclic Chem., 1969, 6(5), 671–679.

Wojciechowska, H. et al., "Preparation of 2,4–dinitrophenyl derivatives of tyrosine," Chemical Abstracts, 1968, 68(25), Abstract No. 114926r, 1 page.

Lobb, R.R., et al., "Small molecule antagonists of alpha4 integrins: novel drugs for asthma," Exp. Opin, Invest. Drugs, 1999, XP000885957, 8(7), 935–945.

Samanen, J., et al., "Vascular indications for integrin alpha V antagonists," Current Pharm. Design., 1997, 3, 545–584.

Šavrda, J., "CIS–TRANS isomerism of N–ACYL derivatives of proline and its analogues, linear peptides with CIS peptide bonds," Proc. 14$^{th}$ European Peptide Symposium, Loffet, A. (ed.), 1976, 653–656.

* cited by examiner

PHENYLALANINE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been subdivided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A Current Topics in Microbiology and Immunology, 184, 7, (1993)]. The members of the family are typically named according to their heterodimer composition although trivial nomenclature is widespread in this field. Thus the integrin termed $\alpha_4\beta_1$ consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised.

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the $\alpha 4$ chain which can pair with two different beta chains $\beta 1$ and $\beta 7$ [Sonnenberg, A. ibid]. The $\alpha_4\beta_1$ pairing occurs on many circulating leukocytes (for example lymphocytes, monocytes and eosinophils) although it is absent or only present at low levels on circulating neutrophils. $\alpha_4\beta_1$ binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between $\alpha_4\beta_1$ and ligands on other cells and the extracellular matrix plays an important role in leukocyte migration and activation [Yednock, T. A. et al, Nature, 356, 63, (1992); Podolsky, D. K et al. J. Clin. Invest. 92, 373, (1993); Abraham, W. M. et al. J. Clin. Invest. 93, 776, (1994)].

The integrin generated by the pairing of $\alpha 4$ and $\beta 7$ has been termed LPAM-1 [Holzmann, B and Weissman, I. EMBO J. 8, 1735, (1989)] and like $\alpha_4\beta_1$ binds to VCAM-1 and fibronectin. In addition, $\alpha_4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha_4\beta_7$ and MAdCAM-1 may also be important at sites of inflammation outside of mucosal tissue [Yang, X-D. et al, PNAS, 91, 12604 (1994)].

Regions of the peptide sequence recognised by $\alpha_4\beta_1$ and $\alpha_4\beta_7$ when they bind to their ligands have been identified. $\alpha_4\beta_1$ seems to recognise LDV, IDA or REDV peptide sequences in fibronectin and a QIDSP sequence in VCAM-1 [Humphries, M. J. et al, ibid] whilst $\alpha_4\beta_7$ recognises a LDT sequence in MAdCAM-1 [Briskin, M. J. et al., J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the $\alpha_4\beta_1$ binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes inhibition of their ligand binding functions can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of the binding of $\alpha 4$ integrins to their ligands. Members of the group are able to inhibit the binding of $\alpha 4$ integrins such as $\alpha_4\beta_1$ and/or $\alpha_4\beta_7$ to their ligands at concentrations at which they generally have no or minimal inhibitory action on $\alpha$ integrins of other subgroups. The compounds are thus of use in medicine, for example in the prophylaxis and treatment of immune or inflammatory disorders as described hereinafter.

Thus according to one aspect of the invention we provide a compound of formula (1)

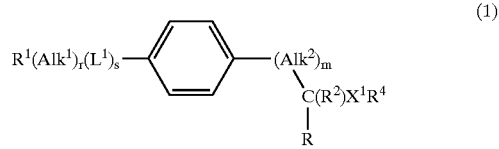

wherein

R is a carboxylic acid ($CO_2H$) or a derivative thereof;

$R^1$ is a hydrogen atom or a hydroxyl, straight or branched alkoxy or optionally substituted cycloaliphatic, polycycloaliphatic, hetero-cycloaliphatic, polyheterocycloaliphatic, aromatic or heteroaromatic group;

$Alk^1$ is an optionally substituted aliphatic or heteroaliphatic chain;

$L^1$ is a linker atom or group;

r and s, which may be the same or different, is each zero or an integer 1 provided-that when r is zero $R^1$ is an optionally substituted cycloaliphatic, polycycloaliphatic, polyheterocycloaliphatic, aromatic or heteroaromatic group;
Alk² is a straight or branched alkylene chain;
m is zero or an integer 1;
R² is a hydrogen atom or a methyl group;
X¹ is a group selected from —N(R³)CO— (where R³ is a hydrogen atom or a straight or branched alkyl group); —N(R³)SO₂—, —N(R³)C(O)O— or —N(R³)CON(R³ᵃ)— (where R³ᵃ is a hydrogen atom or a straight or branched alkyl group);
R⁴ is an optionally substituted aliphatic, cycloaliphatic or polycycloaliphatic group;
and the salts, solvates, hydrates and N-oxides thereof, for use in modulating cell adhesion.

The compounds of formula (1) are potent and selective inhibitors of the binding of α4 integrins to their ligands. The ability of the compounds to act in this way may be simply determined by employing tests such as those described in the Examples hereinafter. In particular compounds of the invention are advantageously selective α4β1 inhibitors.

The compounds of formula (1) are thus of use in modulating cell adhesion and in particular are of use in the prophylaxis and treatment of diseases or disorders involving inflammation in which the extravasation of leukocytes plays a role. The invention extends to such a use and to the use of compounds of formula (1) for the manufacture of a medicament for treating such diseases or disorders. Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds of formula (1) may be administered as pharmaceutical compositions, and according to a further aspect of the invention we provide a pharmaceutical composition which comprises a compound of formula (1) together with one or more pharmaceutically acceptable carriers, excipients or diluents, for use in modulating cell adhesion, particularly in the prophylaxis and treatment of diseases or disorders involving inflammation as just described.

Pharmaceutical compositions for use according to the invention may take a form suitable for oral, buccal, parenteral, nasal, topical or rectal administration, or a form suitable for administration by inhalation or insufflation and the invention extends to the use of a compound of formula (1) in the manufacture of such formulations.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichloro-fluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of formula (1) required for the prophylaxis or treatment of a particular condition will vary depending on the compound chosen, and the condition of the patient to be treated. In general, however, effective daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

Particular compounds of formula (1) form a further feature of the invention and in a further aspect we therefore provide a compound of formula (1a):

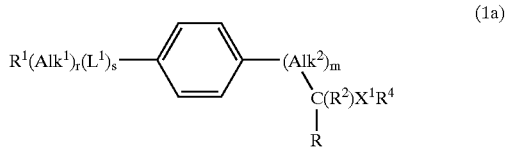

(1a)

wherein
R is a carboxylic acid (—CO₂H) or a derivative thereof;
R¹ is an optionally substituted cycloaliphatic, polycycloaliphatic, heterocycloaliphatic, polyheterocyclialiphatic, aromatic or heteroaromatic group;
Alk¹ is an optionally substituted aliphatic or heteroaliphatic chain;
L¹ is a linker atom or group;
r and s, which may be the same or different, is each zero or an integer 1;
Alk² is a straight or branched alkylene chain;
m is zero or an integer 1;

$R^2$ is a hydrogen atom or a methyl group;

$X^1$ is a group selected from —N($R^3$)CO— (where $R^3$ is a hydrogen atom or a straight or branched alkyl group); —N($R^3$)SO$_2$—, —N($R^3$)C(O)O— or —N($R^3$)CON($R^{3a}$)— (where $R^{3a}$ is a hydrogen atom or a straight or branched alkyl group);

$R^4$ is an optionally substituted aliphatic, cycloaliphatic or polycycloaliphatic group;

and the salts, solvates, hydrates and N-oxides thereof.

It will be appreciated that compounds of formulae (1) and (1a) may have one or more chiral centres. Where one or more chiral centres is present, enantiomers or diastereomers may exist, and the invention is to be understood to extend to all such enantiomers, diastereomers and mixtures thereof, including racemates. Formulae (1) and (1a) and the formulae hereinafter are intended to represent all individual isomers and mixtures thereof, unless stated or shown otherwise.

In the compounds of formulae (1) and (1a), derivatives of the carboxylic acid group R include carboxylic acid esters and amides. Particular esters and amides include those —CO$_2$R$^{5a}$ and —CON(R$^{5a}$)$_2$ groups described below.

When in the compounds of formulae (1) and (1a) $L^1$ is present as a linker atom or group it may be any divalent linking atom or group. Particular examples include —O— or —S— atoms or —C(O)—, —C(O)O—, —C(S)—, —S(O)—, —S(O)$_2$—, —N(R$^5$)—[where R$^5$ is a hydrogen atom or a straight or branched alkyl group], —CON(R$^5$)—, —OC(O)N(R$^5$)—, —CSN(R$^5$)—, —N(R$^5$)CO—, —N(R$^5$)C(O)O—, —N(R$^5$)CS—, —S(O)N(R$^5$)—, —S(O)$_2$N(R$^5$)—, —N(R$^5$)S(O)—, —N(R$^5$)S(O)$_2$—, —N(R$^5$)CON(R$^5$)—, —N(R$^5$)CSN(R$^5$)—, —N(R$^5$)SON(R$^5$)— or —N(R$^5$)SO$_2$N(R$^5$)— groups. Where the linker group contains two $R^5$ substituents, these may be the same or different.

Alk$^2$ in the compounds of formulae (1) and (1a) may be for example a straight or branched C$_{1-3}$alkylene chain. Particular examples include —CH$_2$—, —CH(CH$_3$)—, —C(CH$_3$)$_2$— and —(CH$_2$)$_2$—.

When $R^3$, $R^{3a}$ and/or $R^5$ in the compounds of formula (1) is a straight or branched alkyl group it may be a straight or branched C$_{1-6}$ alkyl group, e.g. a C$_{1-3}$ alkyl group such as a methyl or ethyl group.

When Alk$^1$ in compounds of formula (1) is an optionally substituted aliphatic chain it may be an optionally substituted C$_{1-10}$ aliphatic chain. Particular examples include optionally substituted straight or branched C$_{1-6}$ alkylene, C$_{2-6}$ alkenylene, or C$_{2-6}$ alkynylene chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups $L^2$ where $L^2$ is as defined above for $L^1$ when $L^1$ is a linker atom or group. Each $L^2$ atom or group may interrupt the aliphatic chain, or may be positioned at its terminal carbon atom to connect the chain to the atom or group $R^1$.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, (CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups $L^2$ to form an optionally substituted heteroaliphatic chain. Particular examples include optionally substituted —L$^2$CH$_2$—, —CH$_2$L$^2$CH$_2$—, —L$^2$(CH$_2$)$_2$—, —CH$_2$—L$^2$(CH$_2$)$_2$—, —(CH$_2$)$_2$—L$^2$CH$_2$—, —L$^2$(CH$_2$)$_3$— and —(CH$_2$)$_2$L$^2$(CH$_2$)$_2$— chains.

The optional substituents which may be present on aliphatic or heteroaliphatic chains represented by Alk$^1$ include one, two, three or more substituents selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio e.g. methylthio or ethylthio, amino or substituted amino groups. Substituted amino groups include —NHR$^5$ and —N(R$^5$)$_2$ groups where R$^5$ is a straight or branched alkyl group as defined above. Where two R$^5$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— —CH$_2$CH(CF$_3$)—, —CH$_2$C(CF$_3$)$_2$—, —CH(CF$_3$)— and —C(CF$_3$)$_2$CH$_2$-.

Alkoxy groups represented by $R^1$ in compounds of formula (1) include straight of branched C$_{1-6}$alkoxy groups such as methoxy and ethoxy groups.

When $R^1$ is present in compounds of formulae (1) and (1a) as an optionally substituted cycloaliphatic group it may be an optionally substituted C$_{3-10}$ cycloaliphatic group. Particular examples include optionally substituted C$_{3-10}$cycloalkyl, e.g. C$_{3-7}$cycloalkyl, or C$_{3-10}$cycloalkenyl e.g. C$_{3-7}$cycloalkenyl groups.

Optionally substituted heterocycloaliphatic groups represented by $R^1$ include the optionally substituted cycloaliphatic groups just described for $R^1$ but with each group additionally containing one, two, three or four heteroatoms or heteroatom-containing groups $L^2$ as just defined.

Optionally substituted polycycloaliphatic groups represented by $R^1$ include optionally substituted C$_{7-10}$ bi- or tricycloalkyl or C$_{7-10}$bi- or tricycloalkenyl groups. Optionally substituted polyheterocycloaliphatic groups represented by $R^1$ include the optionally substituted polycycloalkyl groups just described, but with each group additionally containing one, two, three or four $L^2$ atoms or groups.

Particular examples of $R^1$ cycloaliphatic, polycycloaliphatic, heterocyclo-aliphatic and polyheterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or oxadiazinyl e.g. 1,3,5-oxodiazinyl groups.

The optional substituents which may be present on the $R^1$ cycloaliphatic, polycycloaliphatic, heterocycloaliphatic or polyheterocycloaliphatic groups include one, two, three or more substituents represented by $R^6$, each $R^6$ substituent being selected from halogen atoms, e.g. fluorine, chlorine, bromine or iodine atoms, or C$_{1-6}$alkyl, e.g. methyl or ethyl, haloC$_{1-6}$alkyl, e.g. halomethyl or haloethyl such as difluoromethyl or trifluoromethyl, optionally substituted by hydroxyl, e.g. —C(OH)(CF$_3$)$_2$, C$_{1-6}$alkoxy, e.g. methoxy or ethoxy, haloC$_{1-6}$alkoxy, e.g. halomethoxy or haloethoxy such as difluoromethoxy or trifluoromethoxy, thiol, C$_{1-6}$alkylthio e.g. methylthio or ethylthio, or -(Alk)$_v$R$^7$ groups in which Alk is a straight or branched C$_{1-3}$alkylene chain, v is zero or an integer 1 and R$^7$ is a —OH, —SH, —N(R$^{5a}$)$_2$, —CN, —CO$_2$R$^{5a}$, —NO$_2$, —CON(R$^{5a}$)$_2$, —CSN(R$^{5a}$)$_2$—COR$^{5a}$, —CSN(R$^{5a}$)$_2$, —N(R$^{5a}$)COR$^{5a}$, —N(R$^{5a}$)CSR$^{5a}$, —SO$_2$N(R$^{5a}$)$_2$, —N(R$^{5a}$)SO$_2$R$^{5a}$, —N(R$^{5a}$)CON(R$^{5a}$)$_2$, —N(R$^{5a}$)CSN(R$^{5a}$) or —N(R$^{5a}$)SO$_2$N(R$^{5a}$)$_2$ group in which R$^{5a}$ is an atom or group as defined herein for R$^5$.

In the compounds of formulae (1) and (1a), optionally substituted aromatic groups represented by the group R$^1$ include for example monocyclic or bicyclic fused ring C$_{6-12}$ aromatic groups, such as phenyl, 1- or 2-naphthyl, 1- or 2-tetrahydronaphthyl, indanyl or indenyl groups, optionally substituted by one, two, three or more R$^6$ atoms or groups as just described for R$^1$ cycloaliphatic groups.

Optionally substituted heteroaromatic groups, represented by the group R$^1$ in compounds of formulae (1) and (1a) include for example optionally substituted C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N—C$_{1-6}$aimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]-benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro] benzopyranyl, quinazolinyl, naphthyridinyl, pyrido[3,4-b] pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on R$^1$ heteroaromatic groups include one, two, three or more R$^6$ atoms or groups as described above for R$^1$ cycloaliphatic groups.

Particular aliphatic groups represented by R$^4$ in compounds of formulae (1) and (1a) include optionally substituted C$_1$-10aliphatic groups. Particular examples include optionally substituted straight or branched C$_{1-6}$alkyl, C$_{2-6}$alkenyl or C$_{2-6}$alkynyl groups. Optional substituents include one, two or three substituents, where each substituent may be the same or different and is selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio, e.g. methylthio or ethylthio, haloC$_{1-6}$alkoxy, e.g. fluoroC$_{1-6}$alkoxy such as difluoromethoxy or trifluoromethoxy, —N(R$^{5b}$)$_2$ [where R$^{5b}$ is as defined above for R$^5$], phenyl, C$_{3-7}$cycloalkyl, C$_{3-7}$cycloalkenyl, C$_{3-7}$cycloalkoxy or C$_{3-7}$cycloalkenoxy groups.

Particular examples of R$^4$ aliphatic groups include optionally substituted —CH$_3$, —CH$_2$CH$_3$, —CH(CH$_3$)$_2$, —C(CH$_3$)$_3$, —(CH$_2$)$_2$CH$_3$, —(CH$_2$)$_3$CH$_3$, —CH(CH$_3$) CH$_2$CH$_3$, —CH$_2$CH(CH$_3$)$_2$, —CH(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CH$_2$CCCH$_3$ or —(CH$_2$)$_2$CCH groups.

When the group R$^4$ in compounds of formula (1) or (1a) is an optionally substituted cycloaliphatic group it may be for example an optionally substituted C$_{3-10}$cycloaliphatic group. Particular examples include optionally substituted C$_{3-10}$cycloalkyl, e.g. C$_{3-7}$cycloalkyl, and C$_{3-10}$cycloalkenyl, e.g. C$_{3-7}$cycloalkenyl groups. Optional substituents include one, two or three substituents, where each substituent may be the same or different and is selected from halogen atoms, e.g. fluorine, chlorine, bromine or iodine atoms, or hydroxyl, C$_{1-6}$alkoxy e.g. methoxy or ethoxy, thiol, C$_{1-6}$alkylthio, e.g. methylthio or ethylthio, C$_{1-6}$alkyl, e.g. methyl or ethyl, haloC$_{1-6}$alkyl e.g. fluoroC$_{1-6}$alkyl such as difluoromethyl or trifluoromethyl, haloC$_{1-6}$ alkoxy, e.g. fluoroC$_{1-6}$alkoxy such as difluoromethoxy or trifluoromethoxy, phenyl or —N(R$^{5b}$)$_2$ groups.

Particular examples of R$^4$ cycloaliphatic groups include optionally substituted cyclopropyl, cyclobutyl, cyclopentyl, cyclohexyl, cycloheptyl, 2-cyclobuten-1-yl, 2-cyclopenten-1-yl and 3-cyclopenten-1-yl groups.

Optionally substituted polycycloaliphatic groups represented by R$^4$ in compounds of formula (1) or (1a) include optionally substituted C$_{7-10}$bi- or tricycloalkyl, e.g. norbornyl or adamantyl, or C$_{7-10}$bi- or tricycloalkenyl, e.g. norbornenyl groups. Optional substituents include one, two or three substituents as described above in relation to cycloaliphatic groups represented by R$^4$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

When present, the aliphatic chain represented by Alk$^1$ in compounds of the invention is preferably a —CH$_2$— chain.

Alk$^2$ in compounds of formulae (1) and (1a) is preferably a —CH$_2$—chain and m is preferably an integer 1.

R$^2$ in compounds of formulae (1) and (1a) is preferably a hydrogen atom.

R$^3$ and R$^{3a}$ in compounds of formulae (1) and (1a) is each preferably a hydrogen atom.

In general in compounds of formulae (1) and (1a) -(Alk$^1$)$_r$(L$^1$)s— is preferably —CH$_2$O— or —CON(R$^5$)—, especially —CONH—.

The group R in compounds of formulae (1) and (1a) is preferably a carboxylic acid (—CO₂H) group.

In general in compounds of formulae (1) and (1a) the group $R^1$ is preferably an optionally substituted aromatic or heteroaromatic group. Particularly useful groups of these types include optionally substituted phenyl, pyridyl or pyrimidinyl groups, particularly those in which the substituent when present is an atom or group $R^6$ as described above.

A particularly useful class of compounds according to the invention has the formula (1b)

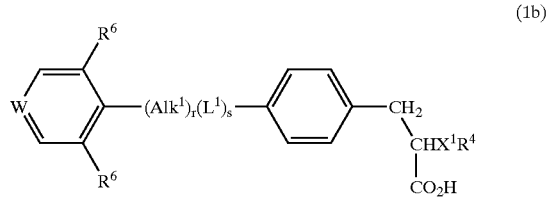

(1b)

wherein —W= is —CH= or —N=, each $R^6$ group may be the same or different and is as generally defined above, and $Alk^1$, r, $L^1$, s, $X^1$ and $R^4$ are as generally defined above, and the salts, solvates, hydrates and N-oxides thereof.

In compounds of formula (1b) -(Alk¹)ᵣ(L¹)ₛ— is preferably a —CH₂O or —CON(R⁵)— group, especially a —CONH— group.

$R^4$ in compounds according to formulae (1), (1a) and (1b) is preferably an optionally substituted straight or branched $C_{1-6}$alkyl group or an optionally substituted $C_{3-7}$cycloalkyl or $C_{7-10}$tricycloalkyl group. Particular examples of such groups include optionally substituted straight or branched $C_{1-4}$alkyl groups as more particularly detined above in relation to compounds of formula (1a), and optionally substituted cyclopropyl, cyclobutyl, cyclopentyl and adamantyl groups.

In one class of compounds according to formula (1), (1a) or (1b) $X^1$ is present as a —N(R³)CO— group where $R^3$ is a hydrogen atom or a straight or branched alkyl group. In compounds of this type $R^4$ may for example be an optionally substituted aliphatic or cycloaliphatic group. In general compounds in which $X^1$ is a —NHCO— group are particularly useful.

Particularly useful comounds according to the invention include:
N-Isopropaloyl-N-(3,5-dichloroisonicotinoyl)-L4-aminophenylalanine;
N-Cyclopropaloyl-N-(3,5-dichloroisonicotinoyl)-L4-aminophenylalanine;
N-Acetyl-N'-(3,5-dichloroisonicotinoyl)-L-4-aminophenylalanine;
N-(Trimethylacetyl)-N'-(2,6-difluorobenzoyl)-L4-aminophenylalanine;
N-(1-Adamantylcarbonyl)-N'-(2,6-dichlorobenzoyl)-L4-aminophenyl alanine;
and the salts, solvates, hydrates and N-oxides thereof.

The compounds of formulae (1) and (1a) may be prepared by a number of processes as generally described below and more specifically in the Examples hereinafter. In the following process description, the symbols $R^1$–$R^4$, $L^1$, $Alk^1$, $Alk^2$, $X^1$, m, r, s and R when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of the desired compound and the processes described hereinafter are to be understood to extend to such removal of protecting groups. For convenience, the processes described below all refer to the preparation of a compound of formula (1) but clearly the description applies equally to the preparation of compounds of formula (1a).

Thus a compound of formula (1) in which R is a —CO₂H group may be obtained by hydrolysis of an ester of formula (2):

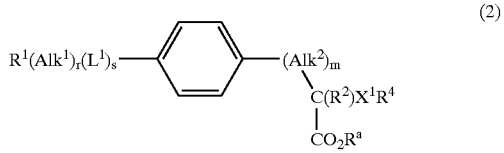

(2)

where $R^a$ is an alkyl group.

The hydrolysis may be performed using either an acid or a base depending on the nature of $R^a$, for example an organic acid such as trifluoroacetic acid or an inorganic base such as lithium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (2) may be prepared by coupling an amine of formula (3):

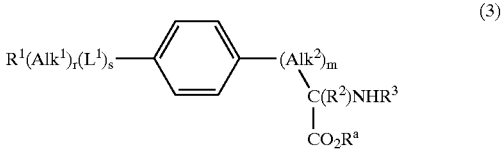

(3)

(where $R^a$ is as just described) or a salt thereof with an acid of formula (4):

R⁴CO₂H   (4)

or an active derivative thereof, a chloroformate R⁴CO₂Cl, a sulphonyl halide R⁴SO₂Hal (where Hal is a halogen atom such as a chlorine atom) or an isocyanate R⁴NCO.

Active derivatives of acids of formula (4) include anhydrides, esters and halides. Particular esters include pentafluorophenyl or succinyl esters.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or dimethyl-aminopyridine, or a cyclic amine, such as N-methylmorpholine.

Where an acid of formula (4) is used, the reaction may additionally be performed in the presence of a condensing agent, for example a diimide such as 1-(3- dimethylaminopropyl)-3-ethylcarbodiimide or N,N'-dicyclo-hexylcarbodiimide, advantageously in the presence of a catalyst such as a N-hydroxy compound e.g. a N-hydroxytriazole such as 1-hydroxy-benzotriazole. Alternatively, the acid may be reacted with a chloroformate, for example ethylchloroformate, prior to reaction with the amine of formula (3).

Intermediates of formulae (2), (3) and (4), or compounds of formula (1), may be manipulated to introduce substituents to aromatic or heteroaromatic groups or modify existing substituents in groups of these types. Typically, such manipulation may involve standard substitution approaches employing for example alkylation, arylation, heteroarylation, acylation, thioacylation, halogenation, sulphonylation, nitration, formylation or coupling reactions. Alternatively, exisiting substituents may be modified for example by oxidation, reduction or cleavage reactions. Particular examples of such reactions are given below.

Thus in one example, a compound wherein $R^1$ $(Alk^1)_r$ $(L^1)_s$— is a —$L^1H$ group may be alkylated, arylated or heteroarylated using a reagent $R^1(Alk^1)_rX$ in which $R^1$ is other than a hydrogen atom and X is a leaving atom or group such as a halogen atom, e.g. a fluorine, bromine, iodine or chlorine atom or a sulphonyloxy group such as an alkylsulphonyloxy, e.g. trifluoro-methylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydro-furan.

In another example, a compound where $R^1$ $(Alk^1)_r(L^1)_s$ is a —$L^1H$ group is a hydrogen atom may be functionalised by acylation or thioacylation, for example by reaction with a reagent $R^1(Alk^1)_rL^1X$ [wherein $L^1$ is a —C(O)—, C(S)—, —N($R^4$)C(O)— or N($R^4$)C(S)— group], in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature, or by reaction with $R^1(Alk^1)_rCO_2H$ or an activated derivative thereof, for example as described above for the preparation of esters of formula (2).

In a further example a compound may be obtained by sulphonylation of a compound where $R^1$ $(Alk^1)_r(L^1)_s$ is an —OH group by reaction with a reagent $R^1$ $(Alk^1)_rL^1$ Hal [in which $L^1$ is —S(O)— or —$SO_2$— and Hal is a halogen atom such as chlorine atom] in the presence of a base, for example an inorganic base such as sodium hydride in a solvent such as an amide, e.g. a substituted amide such as dimethylformamide at for example ambient temperature.

In another example, a compound where $R^1(Alk^1)_r(L^1)_s$ is a —$L^1H$ group, may be coupled with a reagent $R^1OH$ (where $R^1$ is other than a hydrogen atom) or $R^1Alk^1OH$ in a solvent such as tetrahydrofuran in the presence of a phosphine, e.g. triphenylphosphine and an activator such as diethyl, diisopropyl- or dimethylazodicarboxylate to yield a compound containing a $R^1$ $(Alk^1)_rO$— group.

In a further example, ester groups —$CO_2R^4$ or —$CO_2Alk^4$ in compounds of formula (1) may be converted to the corresponding acid [$CO_2H$] by acid- or base-catalysed hydrolysis depending on the nature of the grousp $R^4$ or $Alk^4$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxane or an alkali metal hydroxide, e.g. lithium, hydroxide in an aqueous alcohol, e.g. aqueous methanol.

In a second example, —$OR^7$ [where $R^7$ represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^7$ group (where $R^7$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^4$ or $CO_2R^4$] or aldehyde [—CHO] by reduction, using for example a complex metal hydride such as lithium aluminium hydride or sodium borohydride in a solvent such as methanol.

In another example, alcohol —OH groups in compounds of formula (1) may be converted to a corresponding —$OR^3$ group by coupling with a reagent $R^7OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in compounds of the invention, for example when present in the linker group $L^1$ may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature.

Intermediates of formulae (3) and (4), $R^4CO_2Cl$, $R^4SO_2Hal$, $R^4NCO$, $R^1(Alk^1)_rX$, $R^1(Alk^1)_rL^1X$, $R^1(Alk^1)_rCO_2H$, $R^1OH$ and $R^1Alk^1OH$ are either known compounds or may be prepared from known starting materials by use of analogous processes to those used for the preparation of the known compounds and/or by treating known compounds by one or more of the alkylation, acylation and other manipulations described herein.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. All temperatures are in ° C. The following abbreviations are used:

| | |
|---|---|
| EDC | 1-(3-dimethylaminopropyl)3-ethycarbodiimide; |
| DMF | dimethylformamide; |
| NMM | N-methylmorpholine; |
| DMSO | dimethylsulphoxide; |
| Et | ethyl; |
| HOBT | 1-hydroxybenzotriazole; |
| Boc | tert-butoxycarbonyl; |
| Ar | aryl; |

INTERMEDIATE 1 used in the following Examples is N'-(3,5-dichloro-isonicotinoyl)-L-4-aminophenylalanine methyl ester prepared from 3,5-dichloroisonicotinoyl chloride and N-Boc-L-4-aminophenylalanine methyl ester.

INTERMEDIATE 2

N-Boc-N'-(2,6-Difluorobenzoyl)-L-4-aminophenylalanine Methyl Ester

A mixture of 2,6-difluorobenzoic acid (10 g, 63.3 mmol) and DMF (3 drops) in dichloromethane (150 ml) was treated with thionyl chloride (23 ml, 316.5 mmol). The mixture was heated at reflux overnight. The solvent was removed in vacuo and the residue azeotroped (toluene 3×50 ml) to give 2,6-difluorobenzoyl chloride as an oil (8.59 g, 77%). N Boc-L4-aminophenylalanine methyl ester (100.92 g, 40.6 mmol) and NMM (5.3 ml, 48.7 mmol) were added to a solution of the above acid chloride in DMF (50 nm). The mixture was stirred at room temperature for 2 h. The solvent was removed in vacuo and the residue partitioned between ethyl acetate and aqueous. The aqueous layer was extracted with ethyl acetate (3×100 ml). The combined organic layers were dried ($MgSO_4$) and evaporated in vacuo to give a pale brown oily solid. Trituration with ether gave the title compound as a white solid (6.93 g). $\delta_H(d^6$ DMSO) 7.67–7.53 (3H, m), 7.27–7.20 (5H, m), 4.19–4.11 (1H, m), 3.62 (3H, s), 3.00–2.73 (2H, m), 1.33 (9H, s); m/z (ESI, 70V) 457 (M++Na).

INTERMEDIATE 3

N'-(2,6-Difluorobenzoyl)-L-4-aminophenylalanine Methyl Ester Hydrochloride

A slurry of Intermediate 2 (6.93 g) in 1M HCl/ethyl acetate (100 ml) was stirred at room temperature for 3 h. The solvent was removed in vacuo, ethyl acetate was added to the residue and the solid filtered off and dried to give the title compound as a white solid (6.0 g). $\delta_H(d^6$ DMSO) 10.86 (1H, s), 8.73 (2H, br s), 7.65 (2H, d, J 6.5 Hz), 7.63–7.55 (1H, m), 7.26–7.21 (4H, m), 4.23 (1H, t, J 6.6 Hz), 3.70 (3H, s), 3.17–3.12 (2H, m); m/z (ESI, 70V) 335 (M⁺+H).

INTERMEDIATE 4

N-(Trimethylacetyl)-L-4-nitrophenylalanine Methyl Ester

Trimethylacetyl chloride (17.75 ml, 1.1 eq) was added dropwise over 15 min to a solution of L-4-nitrophenylalanine methyl ester hydrochloride (30 g, 131 mmol) and NMM (31.7 ml, 2.2 eq) in DMF (300 ml) at 0°. Dimethylaminopyridine (catalytic) was added and the reaction mixture stirred at room temperature overnight. The solvent was removed in vacuo and the residue dissolved in ethyl acetate (500 ml). This solution was washed with aqueous $NaHCO_3$ (300 ml), citric acid (10%, 2×300 ml), aqueous $NaHCO_3$ (500 ml) and brine (500 ml), dried ($MgSO_4$) and concentrated in vacuo to give the title compound as a brown oil (34.15 g, 85%) $\delta_H(CDCl_3)$ 8.1 (2H, d, J 9.0 Hz), 7.26 (2H, d, J 9.0 Hz), 6.16 (1H, m), 4.8 (1H, q), 3.72 (3H, s), 3.3 (1H, m), 3.2 (1H, m), 1.13 (9H, s); m/z (ESI, 70V) 309 (M⁺+H).

INTERMEDIATE 5

N-(Trimethylacetyl)-L-4-aminophenylalanine Methyl Ester

Palladium on charcoal (10% Pd, 3.0 g) was added to solution of Intermediate 4 (34.15 g, 110 mmol) in methanol (1000 ml) (degassed and under $N_2$). The mixture was stirred under a hydrogen atmosphere (balloon) at room temperature overnight. The catalyst was filtered off and the filtrate concentrated in vacuo to give the title compound (28.32 g, 92%). $\delta_H$ (d⁶ DMSO) 7.5 (1H, d, J 8.0 Hz), 6.84 (2H, d, J 8.0 Hz), 6.45 (2H, d, J 8.0 Hz), 4.85 (2H, t), 4.29 (1H, m), 3.59 (3H, s), 2.8 (2H, m); m/z (ESI, 70V) 279 (M⁺+H).

INTERMEDIATE 6

N-Boc-O—(3,5-dichloroisonicotinyl)-L-tyrosine Methyl Ester

A mixture of N-Boc-L-tyrosine methyl ester (11.95 g, 40.57 mmol), 3,5-dichloro-4-bromethyl pyridine (see International Patent Application No. PCT/GB99/00589; 10.74 g, 44.56 mmol) and caesium carbonate (14.52 g, 44.56 mmol)

in DMF (100 ml) was stirred at room temperature overnight. The solvent was removed in vacuo and the residue partitioned between ethyl acetate and aqueous NaHCO$_3$. The organic layer was washed with citric acid (10%×2), aqueous NaHCO$_3$ (×2) and brine, dried (MgSO$_4$) and concentrated in vacuo to give the title compound as a brown solid (18.0 g, 98%). δ$_H$ (d$^6$ DMSO) 8.72 (2H, s), 7.25 (1H, d, J 8.2 Hz), 7.19 (2H, d, 18.5 Hz), 6.97 (2H, d, 18.5 Hz), 5.20 (2H, s), 4.13 (1H, m), 3.61 (3H, s), 2.95 (1H, dd, J 13.7, 5.0 Hz), 2.82 (1H, m), 1.32 (9H, s) m/z (ESI, 60V) 477 (M$^+$+H).

INTERMEDIATE 7

O-(3,5-Dichloroisonicotinyl)-L-tyrosine Methyl Ester Hydrochloride

Hydrochloric acid (4 M in ethyl acetate, 100 ml) was added to a solution of Intermediate 6 (18 g, 39.6 mmol) in ethyl acetate (100 ml). The mixture was stirred at room temperature for 90 min. The solid formed was filtered off, washed with ethyl acetate and dried to give the title compound as a light brown solid (14.6 g). δ$_H$ (d$^6$ DMSO) 8.79–8.60 (3H, including 2H, s), 7.20 (2H, d, J 8.6 Hz), 7.00 (2H, d, J 8.6 Hz), 7.3–6.9 (2H, v br), 5.21 (2H, s), 4.34–4.20 (1H, m), 3.67 (3H, s), 3.22–3.05 (2H, m); m/z (ESI, 60V) 355 (M$^+$+H).

EXAMPLE 1

N-isopropalolyl-N-(3,5-dichloroisonicotinyl)-L-4-aminophenylalanine Methyl Ester Intermediate 1, hydrochloride salt (1.24 mmol) in DMF (10 ml) was treated successively with NMM (1.1 equivalents, 1.37 mmol), isopropaloyl chloride (1.1 equivalents, 1.37 mmol) and a catalytic amount of 4-dimethylamino-pyridine. The reaction was stirred at 20° for 16 h and evaporated to dryness. The residue was partitioned between 50% sodium hydrogen carbonate and ethyl acetate and the organics washed with 10% citric acid, brine and dried (MgSO$_4$). Evaporation gave the title compound as a white solid. Yield 50%. $^1$HNMR [(CD$_3$)$_2$SO] δH 10.85 (1H, s), 8.78 (2H, s), 8.15 (1H, d, J 8.0 Hz), 7.55 (2H, d, J, 8.5 Hz), 7.22 (2H, d, J 8.5 Hz), 4.45 (1H, m), 3.62 (3H, s), 3.01 (1H, dd, J 13.8, 5.4 Hz), 2.88 (1H, dd, J 13.8, 9.4 Hz), 2.39 (1H, quint, J 6.8 Hz), 0.96 (3H, d, J 6.8 Hz) and 0.90 (3H, d, J 6.8 Hz). m/z (ES+60V) 462, 460 (MNa$^+$, 12, 22%), 440, 438 (MH$^+$, 71, 100%).

The following compounds of Examples 2–4 were prepared in a similar manner.

EXAMPLE 2

N-Cyclopropaloyl-N-(3,5-dichloroisonicotinyl-L-4-aminophenylalanine Methyl Ester from Intermediate 1, hydrochloride salt and cyclopropanecarbonyl chloride. Yield 45%. $^1$HNMR [(CD$_3$)$_2$SO] δH 10.87 (1H, s), 8.79 (2H, s), 8.51 (1H, d, J 7.8 Hz), 7.57 (2H, d, J 8.5 Hz), 7.23 (2H, d, J 8.5 Hz), 4.48 (1H, m), 3.62 (3H, s), 3.00 (1H, dd, J 13.8, 5.7 Hz), 2.89 (1H, dd, J 13.8, 8.9 Hz), 1.62 (1H, m) and 0.63 (4H, m), m/z (ES+60V) 460, 458 (MNa$^+$, 15, 25%), 438, 436 (MH$^+$, 63, 100%).

EXAMPLE 3

N-Pivaloyl-N'-(3,5-dichloroisonicotinoyl)-L-4-aminophenylalanine Methyl Ester from Intermediate 1, hydrochloride salt and pivaloyl chloride. Yield 44%. $^1$HNMR [(CD$_3$)$_2$SO]δH 10.8 (1H, s), 8.79 (2H, s), 7.71 (1H, d, J 8.0 Hz), 7.55 (2H, d, J 8.2 Hz), 7.23 (2H, d, J 8.5 Hz), 4.44 (1H, m), 3.63 (3H, s), 3.06 (1H, dd, J 13.6, 5.4 Hz), 2.97 (1H, dd, J 13.6, 9.6 Hz) and 1.04 (9H, s). m/z (ES+160V) 476, 474 (MNa$^+$, 6, 10%), 454, 452 (MH$^+$, 60, 100%).

EXAMPLE 4

N-("Propanoyl)-N'-(3,5-dichloroisonicotinoyl)-L-4-aminophenyl-alanine Methyl Ester Prepared from Intermediate 1, hydrochloride salt and valeryl chloride as a white solid. δ$_H$ (d$^6$ DMSO) 10.85 (1H, s), 8.79 (2H, s), 8.20 (1H, d, J 8.0 Hz), 7.55 (2H, d, J 8.5 Hz), 7.22 (2H, d, J 8.5 Hz), 4.49 (1H, m), 3.62 (3H, s), 3.02 (1H, dd, J 13.7, 5.3 Hz), 2.85 (1H, dd, J 13.7, 9.6 Hz), 2.06 (2H, t, J 7.3 Hz), 1.38 (2H, m), 1.14 (2H, m), 0.80 (3H, t, J 7.2 Hz); M/z (ESI, 160V) 452 (M$^+$+H).

EXAMPLE 5

N-Isopropaloyl-N-(3,5-dichloroisonicotinoyl)-L4-aminophenylalanine

A solution of the compound of Example 1 (0.5 mmol) in tetrahydrofuran (8 ml) and water (6 ml) was treated with lithium hydroxide dihydrate (1.5 equivalents, 0.75 mmol) and stirred for 4 h at 20°. The reaction was adjusted to pH2 with 2M hydrochloric acid and evaporated to dryness. Trituration of the residue with water gave the title compound as a white solid. Yield 90%. m.p. 257–258°. $^1$HNMR [(CD$_3$)$_2$SO] δH 8.79 (2H, s), 8.00 (1H, d, J 8.1 Hz), 7.55 (2H, d, J 8.5 Hz), 7.23 (2H, d, J 8.5 Hz), 4.40 (1H, m), 3.03 (1H, dd, J 13.7, 4.9 Hz), 2.86 (1H, dd, J 13.7, 9.4 Hz), 2.39 (1H, quint, L6.8 Hz), 0.95 (3H, d, J 6.8 Hz) and 0.89 (3H, d, J 6.8 Hz). m/z (ES+, 60V) 448, 446 (MNa$^+$, 9, 13%), 426, 424 (MH$^+$, 66, 100%).

The following compounds of Examples 5–8 were prepared in a similar manner:

EXAMPLE 6

N—Cyclopropaloyl-N'-(3,5-dichloroisonicotinoyl)-L-4-aminophenylalanine from the compound of Example 2. Yield 78%. m.p. 248–250 °. $^1$HNMR [(CD$_3$)$_2$SO] δH 8.79 (2H, s), 8.36 (1H, d, J 8.1 Hz), 7.56 (2H, d, J 8.5 Hz), 7.24 (2H, d, J 8.5 Hz), 4.43 (1H, m), 3.02 (1H, dd, J 13.8, 52 Hz) 2.86 (1H, dd, J 13.8, 9.1 Hz) and 1.63 (1H, m). m/z (ES+, 60V), 446, 444 (MNa$^+$, 13, 24%), 424, 422 (MH$^+$, 66, 100%).

EXAMPLE 7

N-Pivaloyl-N'-(3,5-dichloroisonicotinoyl)-1-4-aminophenylalanine from the compound of Example 3. Yield 88%. m.p. 125–128 °. $^1$HNMR [(CD$_3$)$_2$SO]δH 10.83 (1H, s), 8.78 (2H, s), 7.53 (3H, m), 7.23 (2H, d, J 8.5 Hz), 4.40 (1H, m), 3.06 (1H, dd, J 13.7, 4.7 Hz), 2.96 (1H, dd, J 13.6, 9.8 Hz) and 1.03 (9H, s). m/z (ES+, 160V) 462, 460 (MNa$^+$, 16, 25%), 440, 438 (MH$^+$, 65, 100%).

EXAMPLE 8

N-("Propanoyl)-N'-(3,5-dichloroisonicotinoyl)-L-4-aminophenyl-alanine from the compound of Example 4 as a white solid, m.p. 242–244 °. δH (d$^6$ DMSO) 12.62 (1H, br s), 10.85 (1H, s), 8.78 (2H, s), 8.06 (1H, d, J 8.2 Hz), 7.56 (2H, d, J 8.5 Hz), 7.23 (2H, d, J 8.5 Hz), 4.43 (1H, m), 3.04 (1H, dd, J 13.7, 4.8 Hz), 2.82 (1H, dd, J9.8 Hz), 2.05 (2H, t. J 7.2 Hz), 1.38 (2H, m), 1.14 (2H, m), 0.80 (3H, t, J 7.2 Hz); m/z (ESI, 60V) 438 (M++H).

EXAMPLE 9

N-Acetyl-N'-(3,5-dichloroisonicotinoyl)-L-4-aminophenylalanine Methyl Ester

A mixture of Intermediate 1, hydrochloride salt (1.24 mmol), HOBT (1.1 equivalents, 1.36 mmol), NMM (2.2 equivalents, 0.3 ml) and glacial acetic acid (1.05 equivalents, 74 µl) were stirred together in DMF (10 ml) during the addition of EDC (1.1 equivalents, 1.36 mmol) and then for 16 h at 20°. The reaction was evaporated and partitioned between ethyl acetate and sodium hydrogen carbonate. The organic phase was washed successively with 10% citric acid (×2), sodium hydrogen carbonate (×1) and brine (×1) and dried ($MgSO_4$). Evaporation gave the title compound as a pale lemon foam in 94% yield. $^1$HNMR [$(CD_3)_2SO$]$\delta$H 10.01 (1H, s), 8.47 (2H, s), 7.54 (2H, d, J 8.5 Hz), 7.01 (2H, d, J 8.5 Hz), 6.47 (1H, d, J 7.9 Hz), 4.75 (1H, m), 3.64 (3H, s), 2.99 (2H, m) and 1.90 (3H, s). m/z (ES+, 160V) 434, 432 ($MNa^+$, 38, 54%), 410 ($MH^+$, 69, 100%).

The following compound of Example 10 was prepared in a similar manner

EXAMPLE 10

N-(1-Phenyl-1-cyclopentanecarbonyl)-N'-2,6-dichlorobenzoyl)-L-4-aminophenylalanine Methyl Ester from N'-(2,6-dichlorobenzoyl)-L-4-aminophenylalanine methyl ester hydrochloride and 1-phenyl-1-cyclopentanecarboxylic acid. $\delta_H$ ($d^6$ DMSO) 7.7–7.4 (6H, m), 7.32–6.92 (8H, m), 4.45 (1H, m), 3.55 (3H, s), 3.1–2.85 (2H, m), 2.6, 2.3 (4H, m), 1.9–1.6 (4H, m), m/z (ESI 60V) 539 ($M^+$+H).

EXAMPLE 11

N-Acetyl-N'-3,5-dichloroisonicotinoyl)-L-4-aminophenylalanine

A solution of the compound of Example 9 (1.1 mmol) in tetrahydrofuran (15 ml) and water (12 ml) was treated with lithium hydroxide (1.5 equivalents, 1.65 mmol) and stirred for 16 h at 20°. The reaction was adjusted to pH2 with 2M hydrochloric acid and evaporated down to a yellow oil. Trituration with water gave the title compound as an off-white solid in 65% yield. m.p. 198–2020. $^1$HNMR [$(CD_3)_2SO$]$\delta$H 10.85 (1H, s), 8.78 (2H, s), 8.15 (1H, d, J 8.0 Hz), 7.55 (2H, d, J 8.5 Hz), 7.22 (2H, d, J 8.5 Hz), 4.39 (1H, m), 3.00 (1H, dd, J 13.8, 5.0 Hz) and 2.82 (1H, dd, J 13.8, 9.3 Hz). m/z (ES+, 160V), 420, 418 ($MNa^+$, 6,9%), 398, 396 ($MH^+$, 47, 100%).

The following compound of Example 12 was prepared in a similar manner:

EXAMPLE 12

N-(1-Phenyl-1-cyclopentanecarbonyl)-N'-2,6-dichlorobenzoyl)-L-4-aminophenylalanine from the compound of Example 10. $\delta_H$ ($d^6$ DMSO) 10.60 (1H, s), 7.59–7.16 (10H, m), 6.98 (2H, d, J 8.4 Hz), 4.40 (1H, m), 3.30–2.7 (2H, m), 2.6–2.4 (4H, m), 1.9–1.5 (4H, m). M/z: (ESI, 60V) 525 ($M^+$+H).

EXAMPLE 13

N-(Trimethylacetyl)-N-2,6-difluorobenzoyl)-L-4-aminophenylalanine Methyl Ester

Trimethylacetyl chloride (443 µl, 3,6 mmol) was added to a solution of Intermediate×23 (1.11 g, 3 mmol) and NMM (395 µl, 3.6 mmol) in DMF (20 ml) at 00. The reaction mixture was stirred at room temperature for 2 h then poured into 1M hydrochloric acid. This mixture was extracted with ethyl acetate (2×50 ml) and the combined extracts washed with aqueous $NaHCO_3$ (2×1 00 ml) and brine (100 ml), dried ($MgSO_4$) and concentrated in vacuo to give the title compound as a white solid (740 mg, 52%). $\delta$H ($d^6$ DMSO) 10.69 (1H, s), 7.68 (1H, d, J 8.0 Hz), 7.67–7.53 (3H, m), 7.26–7.19 (4h, m), 4.46–4.39 (1H, m), 3.62 (3H, s), 3.08–2.88 (2H, m), 1.03 (9H, s); m/z (ESI, 70V) 419 (2++H).

EXAMPLE 14

N-(Trimethylacetyl)-N'-(2,6-difluorobenzoyl)-L-4-aminophenylalanine

Prepared as a white solid, from the compound of Example 13 by ester hydrolysis in a similar manner to the compound of Example 5. m.p. 212–2.18 °. $\delta_H$ ($d^6$ DMSO) 12.58 (1H, br s), 10.69 (1H, s), 7.62–7.48 (4H, m), 7.26–7.19 (4H, m), 4.43–4.35 (1H, m), 3.09–2.91 (2H, m), 1.03 (9H, s); m/z (ESI, 70V) 405 ($M^+$+H).

EXAMPLE 15

N-Trimethylacetyl-N'-(2-chloronicotinoyl)-L-4-aminophenylalanine Methyl Ester

Thionyl chloride (2.48 ml, 10 eq) and DMF (2 drops) were added to a solution of 2-chloronicotinic acid (535 mg, 3.4 mmol) in dichloromethane (3 ml). The mixture was heated at reflux overnight then concentrated in vacuo and azeotroped with toluene (2×5 ml) to give 2-chloronicotinoyl chloride as a yellow oil. A solution of this acid chloride in dichloromethane (5 ml) was added dropwise to a solution of Intermediate 5 (750 mg, 2.69 mmol) and NMM (355 µl, 1.2 eq) in dichloromethane (15 ml) at 00. Dimethylaminopyridine (catalytic) was added and the mixture stirred at room temperature for 2 h. The mixture was then concentrated in vacuo. The residue was dissolved in ethyl acetate (50 ml) and washed with aqueous $NaHCO_3$ (2×50 ml). The organic phase was dried ($MgSO_4$) and concentrated in vacuo, to give the title compound. $\delta_H$ ($CDCl_3$) 10.55 (1H, s), 8.51 (1H, m), 8.05 (1H, m), 7.67 (1H, m), 7.57 (3H, m), 7.2 (2H, m), 4.24 (1H, m), 3.62 (3H, s), 3.08 (2H, m), 1.03 (9H, s); m/z (ESI, 70V) 418 ($M^+$+H).

EXAMPLE 16

N-(Trimethylacetyl)-N'-(2-chloronicotinoyl)-L-4-aminophenylalanine

Prepared from the compound of Example 15 by ester hydrolysis using a similar method to the compound of Example 5. $\delta_H$ ($CDCl_3$) 12.7 (1H, br s), 10.58 (1H, s), 8.52 (1H, m), 8.06 (1H, m), 17.57 (4H, m), 7.21 (2H, m), 4.4 (1H, m), 3.02 (2H, m), 1.03 (9H, s); m/z (ESI, 70V) 404 ($M^+$+H).

EXAMPLE 17

N-(Trimethylacetyl)-N'-(2-chloronicotinoyl)-L-4-aminophenylalanine Methyl Ester

Carbon tetrachloride (1.32 ml, 4 eq) was added to a solution of 2-chloroisonicotinic acid (535 mg, 3.4 mmol)

and triphenylphosphine (1.07 g, 1.2 eq) in tetrahydrofuran (30 ml) and the mixture stirred overnight. A solution of Intermediate 5 (1.13 g, 1.2 eq) in tetrahydrofuran (15 ml) was then added to this crude acid chloride at 0°. NMM (355 µl, 1.2 eq) was added and the mixture stirred overnight. The solvents were removed in vacuo and the residue dissolved in ethyl acetate (50 ml), washed wth hydrochloric acid (2M, 2×10 ml), aqueous NaHCO$_3$ (2×100 ml), water and brine (200 ml). The organic phase was dried (MgSO$_4$) and concentrated in vacuo. Column chromatography (SiO$_2$; ether/hexane, 9:1) gave the title compound as a white solid (290 mg, 20%) $\delta_H$ (CDCl$_3$) 10.5 (1H, s), 9.6 (1H, d, J 5.0 Hz), 7.9 (1H, s), 7.7 (1H, m), 7.6 (3H, m), 7.2 (2H, d, J 8.0 Hz), 4.5 (1H, m), 3.63 (3H, s), 3.07 (2H, m), 1.05 (9H, s); m/z (ESI, 70V) 418 (M$^+$+H).

EXAMPLE 18

N-(Trimethylactyl)-N'-(2-chloroisonicotinoyl)-L-4-aminophenylalanine

Prepared from the compound of Example 17 by ester hydrolysis using a similar method to the compound of Example 5. $\delta_H$ (CDCl$_3$) 12.6 (1H, br s CO$_1$H), 10.5 (1H, s, NH), 8.6 (1H, d); 8.05 (1H, s), 7.9 (1H, m), 7.7 (2H, m), 7.5 (1H, d), 7.3 (2H) 4.45 (1H, m), 305 (1H, m), 2.95 (1H, m), 1.2 (9H, s); m/z (ES++70V); 4.04 (M$^+$—H).

EXAMPLE 19

N-(Trimethylacetyl)-O-(3,5-dichloroisonicotinoyl)-L-tyrosine Methyl Ester

Trimethylacetyl chloride (406 µl, 3.3 mmol) was added to a solution of Intermediate 7 (1.17 g, 3 mmol) and NMM (725 µl, 6.6 mmol) in dichloromethane (50 ml). The mixture was stirred at room temperature for 3 days. Dichloromethane and citric acid (10%) were added, the aqueous layer was extracted with dichloromethane. The combined organic extracts were washed with aqueous NaHCO$_3$ (×2) and brine, dried (MgSO$_4$) and concentrated in vacuo to give the title compound (1.12 g, 86%). $\delta_H$ (d$^6$ DMSO) 8.71 (2H, s), 7.66 (1H, d, J 8.0 Hz), 7.16 (2H, d, J 8.6 Hz), 6.94 (2H, d, J 8.6 Hz), 5.19 (2H, s), 4.45–4.37 (1H, m), 3.61 (3H, s), 3.05–2.89 (2H, m), 1.01 (9H, s); m/z (ESI, 60V) 439 (M$^+$+H).

EXAMPLE 20

N-(Trimethylacetyl)-O-(3,5-dichloroisonicotinoyl)-L-tyrosine

Prepared from the compound of Example 19 by ester hydrolysis using a similar method to the compound of Example 5 to yield a white solid. $\delta_H$ (d$^6$ DMSO) 8.70 (2H, s), 7.45 (1H, d, J 8.6 Hz), 7.16 (2H, d, J 8.6 Hz), 6.94 (2H, d, J 8.6 Hz), 5.18 (2H, s), 4.39–4.34 (1H, m), 3.03 (1H, dd, 113.7, 4.6 Hz), 2.91 (1H, dd, J 13.7, 9,9 Hz), 1.00 (9H, s); m/z (ESI, 60V) 325 (M$^+$+H).

EXAMPLE 21

N-("Butylsulphonyl)-N-(3,5-dichloroisonicotinoyl)-L-4-aminophenylalanine Methyl Ester "Butanesulphonyl chloride (0.17 ml, 1.3 mmol) was added to a solution of Intermediate 1 (500 mg, 1.24 mmol) and diisopropylethylamine (0.7 ml, 3.9 mmol) in dichloromethane (10 ml). The reaction mixture was stirred for 16 h at room temperature, then washed with citric acid (10%), aqueous NaHCO$_3$ and brine, dried (MgSO$_4$) and evaporated in vacuo. Column chromatography (SiO$_2$; ethyl acetate/hexane, 3:1) gave the title compound (120 mg). $\delta_H$ (d$^6$ DMSO) 10.88 (1H, s), 8.79 (2H, s), 7.80 (1H, d, J 8.9 Hz), 7.59 (2H, d, J 8.3 Hz), 7.30 (2H, d, J 8.3 Hz), 4.10 (1H, m), 3.67 (3H, s), 3.02 (1H, dd, J 13.7, 4.8 Hz), 2.77 (1H, dd, J 13.6, 10.1 Hz), 2.60 (2H, t, J 8.3 Hz), 1.22 (4H, m), 0.76 (3H, t, J 7.2 Hz); m/z (ESI, 60V) 488 (M$^+$+H).

EXAMPLE 22

N-("Butylsulphonyl)-N'-(3,5-dichloroisonicotinoyl)-L-4-aminophenylalanine

Prepared from the compound of Example 21 by ester hydrolysis using a similar method fo the compound of Example 5 to yield a white solid. m.p. 252–254 °. $\delta_H$ (d$^6$ DMSO) 12.86 (1H, br s), 10.87 (1H, s), 8.79 (2H, s), 7.59 (3H, m+d J 4 Hz), 7.30 (2H, d, J 8.4 Hz), 3.98 (1H, m), 3.04 (1H, dd, J 13.6, 4.7 Hz), 2.75 (1H, dd, J 13.6, 10.2 Hz), 2.56 (2H, m), 1.20 (4H, m), 0.76 (3H, t, J 7.2 Hz); m/z (ESI 60V) 474 (M$^+$+H).

EXAMPLE 23

N-(α-Sulphonyltoluene)-0-(2,6-dichlorobenzyl)L-tyrosine Methyl Ester

To O-2,6-dichlorobenzyl)-L-tyrosine methyl ester hydrochloride (0.5 gm, 1.3 mmol) in ethyl acetate (10 ml), was added saturated sodium bicarbonate solution (5 ml). The mixture was stirred for 15 min before isolating the organic layer and extracting the aqueous layer with ethyl acetate (3×3 ml). The combined organic solutions were washed with brine (2×5 ml), dried (MgSO$_4$), and the solvent evaporated in vacuo. The residue was dissolved in anhydrous pyridine (3 ml) and cooled in an ice/water bath before the dropwise addition of α-toluene sulphonyl chloride (243 mg, 1.3 mmol). After complete addition the cooling bath was removed and the solution stirred at room temperature for 16 h, before pouring onto water (30 ml) and extracting the product with ethyl acetate (2×20 ml). The combined extracts were washed with water (3×1 0 ml), dried (MgSO$_4$), and solvent removed in vacuo. Column chromatography (SiO$_2$, ethyl acetate/hexane, 1:1) gave the title compound as a viscous yellow oil. $\delta_H$ (CD$_3$OD) 7.36–7.20 (4H, m), 7.00 (2H, d, J 8.8 Hz), 6.90 (2H, d, J 8.8 Hz), 4.74 (1H, d, J 8.9 Hz), 4.1 (3H, m), 3.72 (3H, s), 2.94 (2H, d, J 5.9 Hz); m/z (ESI, 60V) 525 (NH$_4$ adduct).

EXAMPLE 24

N-(αSulphonyltoluene)-O-(2,6-dichlorobenzyl)-L-tyrosine

To the compound of Example 23 (220 mg, 0.43 mmol) dissolved in water (5 ml) and tetrahydrofuran (10 ml) was added lithium hydroxide monohydrate (27 mg, 1.5 equiv). The resulting solution was stirred at room temperature for 2 h. The organic solvent was removed in vacuo and the residue dissolved in water. This solution was acidified with dilute hydrochloric acid and the product extracted into ethyl acetate (3×5 ml), the combined extracts were washed water (2×4 ml), dried (Mg$_2$SO$_4$), and the solvent removed to yield the title compound as a white powder. $\delta_H$ (CDCl$_3$) 7.35–7.21 (8H, m), 7.1 (2H, d, J 7.7 Hz), 6.9 (2H, d, J 7.7 Hz), 4.6 (1H, d, J 8.9 Hz), 4.1 (3H, m,), 3.0 (2H, m). m/z (ESI 60V) 511 (NH$_4$ adduct).

EXAMPLE 25

N-("Propanesulphonyl)-N'-(3,5-dichloroisonicotinoyl)-L-4-aminophenylalanine Methyl Ester The title compound was prepared as a white solid from Intermediate 1 and propanesulphonyl chloride in a similar manner to the compound of Example 21. $\delta_H$ (d$^6$ DMSO) 10.87 (1H, s), 8.78 (2H, s), 7.8 1(1H, d, J 9.0 Hz), 7.59 (2H, d, J 8.4 Hz), 7.29 (2H, d, J 8.4 Hz), 4.09 (1H, br m), 3.67 (3H, s), 3.04 (1H, dd, J 13.7, 5.3 Hz), 2.78 (1H, dd, J 13.7, 9.8 Hz), 2.59 (2H, m), 1.42–1.30 (2H, br m) and 0.76 (3H, t, J 7.3 Hz); m/z (ESI, 60V) 474 (M$^+$+H).

EXAMPLE 26

N-("Prepanesulphonyl)-N'-(3,5-dichloroisonicotinoyl)-L-4-aminophenylalanine

Prepared from the compound of Example 25 by ester hydrolysis in a similar manner to the compound of Example to yield a white solid. $\delta_H$ (d$^6$ DMSO) 10.86 (1H, s), 8.78 (2H, s), 7.58 (2H, d, J 8.3 Hz), 7.30 (2H, d, J 8.3 Hz), 3.98 (1H, m), 3.03 (1H, dd, J 13.6, 6.9 Hz), 2.76: (1H, dd, J 13.6, 9.1 Hz), 2.58 (2H, m), 1.44–1.32 (2H, m) and 0.76 (3H, t, J 7.4 Hz); m/z (ESI, 60V), 460 (M$^+$+H).

EXAMPLE 27

N-(Benzyloxycarbonyl)-N'-(3,5-dichloroisonicotinoyl)-L-4-aminophenylalanine Methyl Ester Benzyl chloroformate (0.32 ml, 2.22 mmol) was added to a solution of Intermediate 1 (750 mg, 1.85 mmol) diisopropylethylamine (0.81 ml, 4.64 mmol) and dimethylaminopyridine (catalytic) in dichloromethane (20 ml) at 0°. The reaction mixture was stirred for 48 h at room temperature, then washed with citric acid (10%), aqueous NaHCO$_3$ and brine, dried (MgSO$_4$) and evaporated in vacuo to give an oil solid.

Trituration (ethyl acetate/hexane, 1:1) gave the title compound as a white solid (225 mg). $\delta_H$ (d$^6$ DMSO) 10.88 (1H, s), 8.80 (2H, s), 7.82 (1H, d, J 8.2 Hz), 7.572H, d, J 8.5 Hz), 7.32 (7H, m), 4.98 (2H, s), 4.28 (1H, m), 3.65 (3H, s), 3.05 (1H, dd, J 13.7, 4.9 Hz), 2.85 (1H, dd, J 13.7, 10.3 Hz); m/z (ESI 60V) 502 (M$^+$+H).

EXAMPLE 28

N-(Benzyloxycarbonyl)-N'-(3,5-dichloroixonicotinoyl)-L-4-aminophenylalanine

Prepared from the compound of Example 27 by ester hydrolysis in a similar manner to the compound of Example 5. $\delta_H$ (d$^6$ DMSO) 12.72 (1H, br s), 10.87 (1H, s), 8.80 (2H, s), 7.65 (1H, d, J 8.5 Hz), 7.57 (2H, d, J 8.5 Hz), 7.28 (7H, m), 4.19 (1H, m), 3.06 (1H, dd, J 15.0, 5.5 Hz), 2.82 (1H, dd, J 15.0, 10.5 Hz); m/z (ESI, 160V) 488 (M$^+$+H).

EXAMPLE 29

N-(Ethoxycarbonyl)-N'-(3,5-dichloroisonicotinoyl)-L-4-aminophenylalanine Methyl Ester Prepared as an off-white solid from Intermediate 1 and ethyl chloroformate in a similar manner to the compound of Example 27. $\delta_H$ (CDCl$_3$) 8.56 (2H, s), 7.63 (1H, br s), 7.54 (2H, d, J 8.5 Hz), 7.16 (2H, m), 5.16 (1H, br s), 4.64 (1H, m), 4.10 (2H, q, J 7.1 Hz), 3.75 (3H, s), 3.11 (2H, m), 1.23 (3H, t, J 7.1 Hz); m/z (ESI, 60V) 440 (M$^+$+H).

EXAMPLE 30

N-(Ethoxycarbonyl)-N'-(3,5-dichloroisonicotinoyl)-L-4-aminophenylalanine

Prepared as a white solid from the compound of Example 30 by ester hydrolysis in a similar manner to the compound of Example 5. $\delta_H$ (d$^6$ DMSO) 10.86 (1H, s), 8.79 (2H, d, J 0.74 Hz), 7.56 (2H, d, J 8.4 Hz), 7.41 (1H, d, J 8.4 Hz), 7.26 (2H, d, J 8.4 Hz), 4.13 (1H, m), 3.93 (2H, m), 3.03 (1H, dd, J 13.7, 4.5 Hz), 2.80 (1H, dd, J 13.6, 10.6 Hz), 1.12 (3H, t, J 7.1 Hz); m/z (ESI, 60V) 426 (M$^+$+H).

EXAMPLE 31

N-(1-Adamantylcarbonyl)-N'-(2,6-dichlorobenzoyl)-L-4-aminophenylalanine Methyl Ester Prepared as a white solid from N'-(2,6-dichlorobenzoyl)-L-4-aminophenyl-alanine methyl ester hydrochloride and 1-adamantanecarbonyl chloride by a method similar to that of Example 1. $\delta_H$ (CDCl$_3$) 7.5 (2H, d, J 8.5 Hz), 7.5–7.3 (4H, m), 7.1 (2H, d, 18.5 Hz), 6.1 (1H, broad d), 4.8 (1H, m), 3.7 (3H, s), 3.1 (2H, m), 2.0 (3H, broad s), 1.8 (6H, broad s), 1.7 (6H, broad s). m/z (ESI 60V) 529 (M$^+$+H).

EXAMPLE 32

N-(1-Adamantylcarbonyl)-N'-(2,6-dichlorobenzoyl)-L-4-aminophenyl Alanine

Prepared from the compound of Example 31 by ester hydrolysis in a similar manner to the compound of Example 5. $\delta_{H\,(d}{}^6$ DMSO) 10.6 (1H, s), 7.7–7.3 (5H, m), 7.2 (2H, d, J 8.2 Hz), 4.5–4.3 (1H, m), 3.2–2.9 (2H, m), 2.0 (3H, broad s), 1.8–1.6 (12H, two broad s). m/z (ESI 60V) 515 (M$^+$+H).

The following compounds of Examples 33 and 34 were prepared by hydrolysis of the corresponding ester in a similar manner to the compound of Example 5:

EXAMPLE 33

N-(2,6-Dichlorophenylacetoyl)-N'-2,6-dichlorobenzoyl)-L-4-aminophenylalanine

The ester starting material was prepared from N'-(2,6-dichlorobenzoyl)-L-4-aminophenylalanine methyl ester hydrochloride and 2,6-dichlorophenylacetyl chloride by a method similar to that of Example 1. $\delta_H$ (d$^6$ DMSO) 10.66 (1H, s, NH), 8.37 (1H, dd, J 8.1 Hz, NH), 7.60–7.20 (10H, m, Ar—H), 4.42 (1H, m, α—CH), 3.79 (2H, m, CH$_2$Ar), 3.05 (1H, dd, J 13.7, 5.0 Hz, CHCH$_A$H$_B$), 2.98 (1H, m, CHCH$_A$H$_B$). m/z (ESI 60V) 538 (MH$^+$).

EXAMPLE 34

N-(Diphenylacetoyl)-N'-(2,6-dichlorobenzoyl)-L-4-aminophenyl Alanine

The ester starting material was prepared from N'-2,6-dichlorobenzoyl)-L-4-aminophenylalanine methyl ester hydrochloride and diphenylacetyl chloride by a method similar to that of Example 1. $\delta_H$ (d$^6$ DMSO) 10.67 1 H, s, NH), 8.55 (1H, d, J 8.2 Hz, NH), 7.61–6.97 (17H, m, Ar—H), 5.01 (1H, s, CHAr$_2$), 4.53 (1H, m, α—CH), 3.05 (1H, m, CHCH$_A$H$_B$), 2.84 (1H, m, CHCH$_A$H$_B$). m/z (ESI, 60V), 547 (MH$^+$).

EXAMPLE 35

N-(Ethylaminocarbonyl)-N'-(3,5-dichloroisonicotinoyl)-L-4-aminophenylalanine Methyl Ester A solution of Intermediate 1 hydrochloride (0.39 g, 1 mmol) and NMM (0.13 ml, 1.2 mmol) in tetrahydrofuran (10 ml) was treated with ethyl isocyanate (0.079 ml, 1.1 mmol) and the reaction stirred overnight at room temperature. The mixture was partitioned between dichloromethane (20 ml) and water (20 ml), the aqueous layer exfracted with dichloromethane (20 ml) and the combined organic layers dried (MgSO$_4$) and concentrated in vacuo to give the title compound as a white solid, 0.29, 66% which was used without further purification.

EXAMPLE 36

N-(Ethylaminocarbonyl)-N'-dichloroisonicotinoyl)-L-4-aminophenylalanine

A solution of the compound of Example 35 (0.29 g, 0.66 mmol) in tetrahydrofuran (5 ml) and water (5 ml) was treated with LiOH.H$_2$O (42 mg, 1.0 mmol) and stirred overnight at room temperature. The reaction mixture was acidified to pH 1 with 10% hydrochloric acid and the resulting white solid isolated by filtration, washed with water (2×1 0 ml) and dried in vacuo to give the title compound 0.22 g, 78%. $\delta_H$ (d$^6$ DMSO) 10.87 (1H, s, NH), 8.79 (2H, s, pyr-H), 7.97 (2H, d, J 8.5 Hz, Ar—H), 7.19 (2H, d, J 8.5 Hz, Ar—H), 6.04 (1H, m, NHEt), 5.97 (1H, d, J 8.4 Hz, CHNH), 4.34 (1H, m, α—CH), 3.02–2.94 (3H, m, CHCH$_A$H$_B$+CH$_2$CH$_3$), 2.85 (1H, dd, J 13.8, 7.6 Hz, CHCH$_A$H$_B$), 0.96 (3H, t, J 7.2 Hz, CH$_2$CH$_3$). m/z (ESI, 70V) 425 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Integrin-Dependant Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 µl at 2 µg/ml in 0.1 M NaHCO$_3$, pH 8.4], overnight at 40. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 µl containing 2.5×10$^5$ Jurkat cells in the presence or absence of titrated test compounds.

Each plate was washed (2×) with medium and the adherent cells were fixed with 100 µl methanol for 10 minutes followed by another wash. 100 µl 0.25% Rose Bengal (Sigma R4507) in PBS was added for 5 minutes at room temperature and the plates washed (3×) in PBS. 100 µl 50% (v/v) ethanol in PBS was added and the plates left for 60 min after which the absorbance (570 nm) was measured.

α4β7 integrin-dependant JY cell adhesion to MAdCAM-Ig

This assay was performed in the same manner as the α$_4$β$_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the α4β1 integrin assay.

α$_5$β$_1$ Integrin-Dependent K562 Cell Adhesion to Fibronectin 96 well tissue culture plates were coated with human plasma fibronectin (Sigma F0895) at 5 µg/ml in phosphate-buffered saline (PBS) for 2 hr at 37° C. The plates were washed (3× in PBS) and then blocked for 1 h in 100 µl PBS/1% BSA at room temperature on a rocking platform. The blocked plates were washed (3× in PBS) and the assay then performed at 37° C. in a total volume of 200 µl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 µl in the presence of 10 ng/ml phorbol-12-myristate-13-acetate, and in the presence or absence of test compounds, and incubated for 20 min at 37° C. followed by 30 min at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 µg/ml TMB (Boehringer Mannheim) in 0.1 M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 µM ADP (Sigma) in the presence or absence of inhibitors.

In the above assays the compounds of the invention generally have IC$_{50}$ values in the α$_4$β$_1$ and α$_4$β$_7$ assays of 1 µM and below. The compounds of the Examples typically had IC$_{50}$ values of 100 nM and below in these assays and demonstrated selective inhibition of α$_4$β$_1$. In the other assays featuring α integrins of other subgroups the same compounds had IC$_{50}$ values of 50 µM and above thus demonstrating the potency and selectivity of their action against α$_4$ integrins.

What is claimed is:
1. A compound of formula (1a):

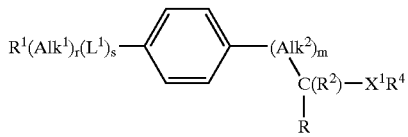

wherein:
R is a carboxylic acid;
R$^1$ is a pyridyl group substituted by one or two halogen atoms;
-(Alk$^1$)$_r$(L$^1$)$_s$— is a —CH$_2$O— or —CON(R$^5$)— group;
R$^5$ is a hydrogen atom or a straight or branched alkyl group;
Alk$^2$ is a straight or branched alkylene chain;

m is zero or an integer 1;

$R^2$ is a hydrogen atom or a methyl group;

$X^1$ is a group selected from —N($R^3$)CO—, (where $R^3$ is a hydrogen atom or a straight or branched alkyl group); —N($R^3$)SO$_2$—, —N($R^3$)C(O)O— or —N($R^3$)CON($R^{3a}$)— (where $R^{3a}$ is a hydrogen atom or a straight or branched alkyl group);

$R^4$ is a straight or branched $C_{1-6}$ alkyl group;

or a pharmaceutically acceptable salt thereof.

2. A compound according to claim 1 wherein -(Alk$^1$)$_r$-(L$^1$)$_s$—is a —CONH— group.

3. A compound according to claim 1 wherein Alk$^2$ is —CH$_2$—, m is an integer 1, and $R^2$ is a hydrogen atom.

4. A compound according to claim 1 wherein $X^1$ is a —NHCO—, —NHSO$_2$—, —NHCO(O)O— or NHCONH— group.

5. A compound according to claim 4 wherein $X^1$ is a —NHCO— group.

6. A compound according to claim 1 wherein $R^4$ is a straight or branched $C_{1-4}$alkyl group.

7. A compound which is selected from the group consisting of:

N-Isopropaloyl-N-(3,5-dichloroisonicotinoyl)-L-4-aminophenylalanine;

N-Cyclopropaloyl-N-(3,5-dichloroisonicotinoyl)-L-4-aminophenylalanine; and N-Acetyl-N'-(3,5-dichloroisonicotinoyl)-L-4-aminophenylalanine;

or a pharmaceutically acceptable salt thereof.

8. A pharmaceutical composition comprising a compound according to claim 1 together with one or more pharmaceutically acceptable carriers, excipients or diluents.

9. A compound according to claim 1 wherein $R^1$ is a pyridyl group substituted by one or two chlorine atoms.

* * * * *